United States Patent
Zimmermann

(10) Patent No.: US 7,242,186 B2
(45) Date of Patent: Jul. 10, 2007

(54) DEVICE FOR TESTING A TEST SPECIMEN FOR SURFACE FAULTS BY MAGNETIZATION MEANS AND BY MEANS OF INDUCTION PROBES AS MEASUREMENT SENSORS

(75) Inventor: Bernd Zimmermann, Koblenz (DE)

(73) Assignee: Prüftechnik Dieter Busch AG, Ismaning (DE)

( * ) Notice: Subject to any disclaimer, the term of this patent is extended or adjusted under 35 U.S.C. 154(b) by 0 days.

(21) Appl. No.: 11/370,166

(22) Filed: Mar. 8, 2006

(65) Prior Publication Data

US 2007/0052413 A1    Mar. 8, 2007

(51) Int. Cl.
*G01N 27/72* (2006.01)
*G01N 27/82* (2006.01)
*G01R 33/12* (2006.01)

(52) U.S. Cl. .................. 324/242; 324/228; 324/243
(58) Field of Classification Search ............. 324/228, 324/232, 238–242, 262
See application file for complete search history.

(56) References Cited

U.S. PATENT DOCUMENTS 5,187,435 A    2/1993  Geweke 5,517,114 A    5/1996  Reitz et al.

FOREIGN PATENT DOCUMENTS

| GB | 2 014 317 A | 8/1979 |
| GB | 2 034 049 A | 5/1980 |
| JP | 10-232222 A | 9/1998 |
| JP | 11-202084 A | 7/1999 |

*Primary Examiner*—Bot LeDynh
(74) *Attorney, Agent, or Firm*—David S. Safran

(57) ABSTRACT

A device for testing a test specimen for surface faults is equipped for delivering a magnetic flux into the specimen and has induction probes measurement sensors. At least two yoke legs have opposed gap-forming ends with oppositely poled exciter coils between which the test specimen can be guided. Outside ends of the yoke legs opposite the gap-forming ends are connected to one another by a magnetic flux conductor so that the magnetic flux runs perpendicular to the lengthwise direction through the test specimen. To adapt to test specimens of different cross section, the yoke legs can be moved and fixed. Testing of test specimens by means of high-energy magnetic alternating fields improved because the high heat losses produced in this process are adequately dissipated. The device is especially well suited to determine the quality of bars, pipes and the like in a hot rolling mill with high-energy alternating magnetic fields.

14 Claims, 2 Drawing Sheets

DEVICE FOR TESTING A TEST SPECIMEN FOR SURFACE FAULTS BY MAGNETIZATION MEANS AND BY MEANS OF INDUCTION PROBES AS MEASUREMENT SENSORS

BACKGROUND OF THE INVENTION

1. Field of the Invention

The invention relates to a device for testing a test specimen for surface faults by magnetization means by delivering a magnetic flux into the specimen and using induction probes as measurement sensors, the induction probes being capable of turning around the specimen, which can be guided in the lengthwise direction, in order to scan it helically.

2. Description of Related Art

These devices are used to determine, for example, surface faults on metallic articles with a round profile, such as billets, bars, steel pipes and the like, while these articles, which can have high temperatures depending on the choice of fabrication process, run through a production line, for example, a mill train.

Magnetization means magnetize the test specimen such that the faults near the surface produce a stray flux which can be detected by means of induction probes. Faults in and under the surface of a test piece cause, for example, a stray flux which is detected by means of induction probes. Therefore, the output signals of the induction probes are a measure of impurities and faults in and under the surface of a test specimen. The induction probes for fault detection are located near the peripheral wall of the test specimen. The induction probes can be suited to detecting magnetic stray flukes or can be designed as eddy current sensors. The induction probes can also operate based on magneto-resistive effects.

German Patent DE 39 37 261 C2 and corresponding U.S. Pat. No. 5,187,435 describe such a device, with a rotating head, for scanning of metallic test material. The rotating head is composed essentially of a housing having a hollow shaft for routing through a test specimen, and having a rotating part to which the induction probes, for example, the eddy current detectors, are attached. Furthermore, there are drive means to produce the peripheral motion of the rotating part. The drive wheel of a drive motor is connected via a drive belt to a drive wheel which sits rigidly on the hollow shaft. On each of the front and back end of the hollow shaft sits a respective protective sleeve, by which the test specimen is guided. A rotating disk is rigidly connected to the hollow shaft. Two levers are pivotally mounted on the hollow shaft and each bears an induction probe. A magnetic flux in the lengthwise direction is routed into the test specimen by means of a magnetization coil which surrounds it and by means of a magnetic flux conductor. Parts of the housing and the hollow shaft are used as the magnetic flux conductor. To homogenize the magnetic field in the test region, there is a homogenization ring of magnetically conductive material.

German Patent Application DE OS 29 05 399 and corresponding UK Patent Application 20 14 317 application disclose another such device and in which a test specimen can be guided by a cylindrical element which can be rotated around its lengthwise axis. Several induction probes, which are made as eddy current fault detector coils, are attached to the cylindrical element near its peripheral wall. By rotating the cylindrical element and simultaneously guiding the test specimen in the lengthwise direction, the specimen is scanned helically by the coils. The output signals of the coils are evaluated in a signal detector circuit. An alternating current signal of fixed frequency is applied to the coils and produces an eddy current a short distance underneath the surface of the test specimen. Faults in the test specimen change the coil impedance. The magnetic flux runs in the test specimen in the lengthwise direction on and underneath the jacket surface of the specimen.

The indicated known devices are subject to the first disadvantage that they cannot be quickly and economically adapted to different dimensions, especially the cross sections, of the test specimens. A second disadvantage lies in the inadequate heat dissipation which, as the third disadvantage, sets narrow limits on the service life of the device, and finally, limits the magnetizing power as the fourth disadvantage. The shape of the coil cores used in the indicated devices can only be changed at high costs for bobbin cores which have been wound insulated.

SUMMARY OF THE INVENTION

Therefore, the object of the invention is to make a device for testing a test specimen for surface faults by magnetization means for delivering a magnetic flux into the specimen and by means of induction probes as measurement sensors such that it can be easily and economically adapted to different test specimens and is characterized by high heat dissipation in order to achieve both high magnetizing power and also service life.

This object is achieved with the features of the invention, in that at least two yoke legs have opposed ends, forming a gap, through which the test specimen can be guided, that on each end there is an exciter coil, that the exciter coils are oppositely poled, that the outside ends of the yoke leg opposite the gap-forming ends are connected to one another by means of the magnetic flux conductor so that the magnetic flux runs perpendicular to the lengthwise direction through the test specimen.

The magnetic flux conductor can be made, for example, triangular, square, or preferably annular. By the measure as claimed in the invention to arrange two yoke legs with one exciter winding each opposite one another such that between the opposing ends, the gap ends, a gap is formed, and to connect the outside ends of the yoke legs to one another via a magnetic flux conductor, this arrangement can be economically produced from a powder composite material and can be adapted to test specimens of different dimensions because the powder composites can be easily worked by sawing, milling and grinding. The outside ends of the yoke legs can rest for example on the magnetic flux conductor. Alternatively the magnetic flux conductor can rest on the outside ends of the yoke legs. The heat loss produced by the remagnetization can be dissipated very well via the magnetic flux conductor. The device as claimed in the invention is therefore suited for high magnetizing powers and is characterized by a long service life.

In order to be able to adapt the device of the invention to test specimens of different cross section, the yoke legs can be moved and fixed in the radial direction; however, the contact with the magnetic flux conductor always remaining independent of the position.

The induction probes, in another embodiment of the invention, sit on levers which are attached to the magnetic flux conductor to be able to pivot around an axis.

Another exemplary embodiment of the invention calls for attaching the preferably annular magnetic flux conductor in a highly heat-conductive manner to a pivoting rotating disk on which there can be cooling louvers or the like for better heat dissipation. To turn the rotating disk, there is a rotary drive.

There can be more than two yoke legs on the magnetic flux conductor, each of which has a respective exciter winding.

The invention is described in greater detail below with reference to the figures of the accompanying drawings.

DETAILED DESCRIPTION OF THE INVENTION

Figure 1:
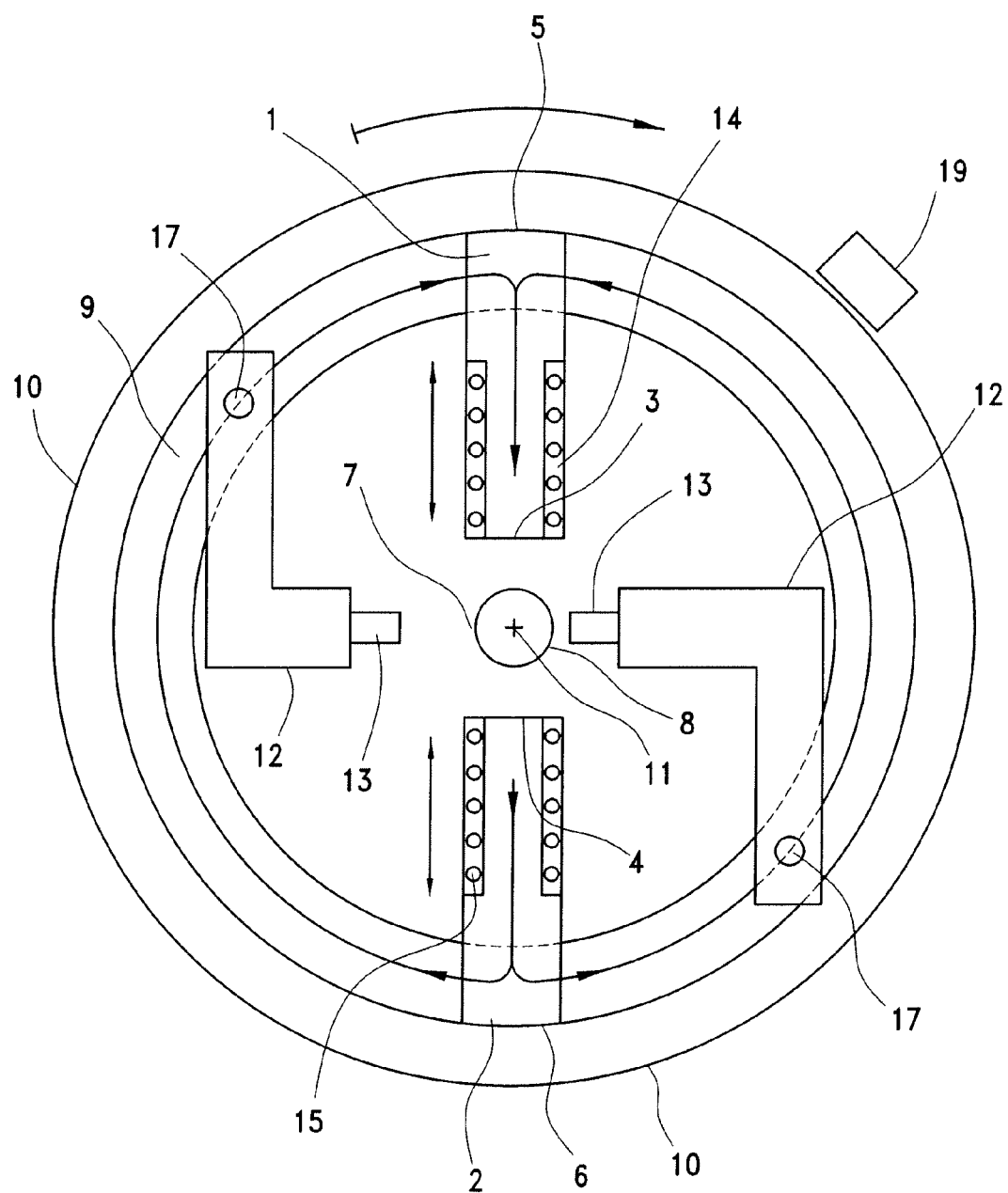
FIG. 1 is a schematic vertical elevational view of an exemplary embodiment of the invention.
Figure 2:
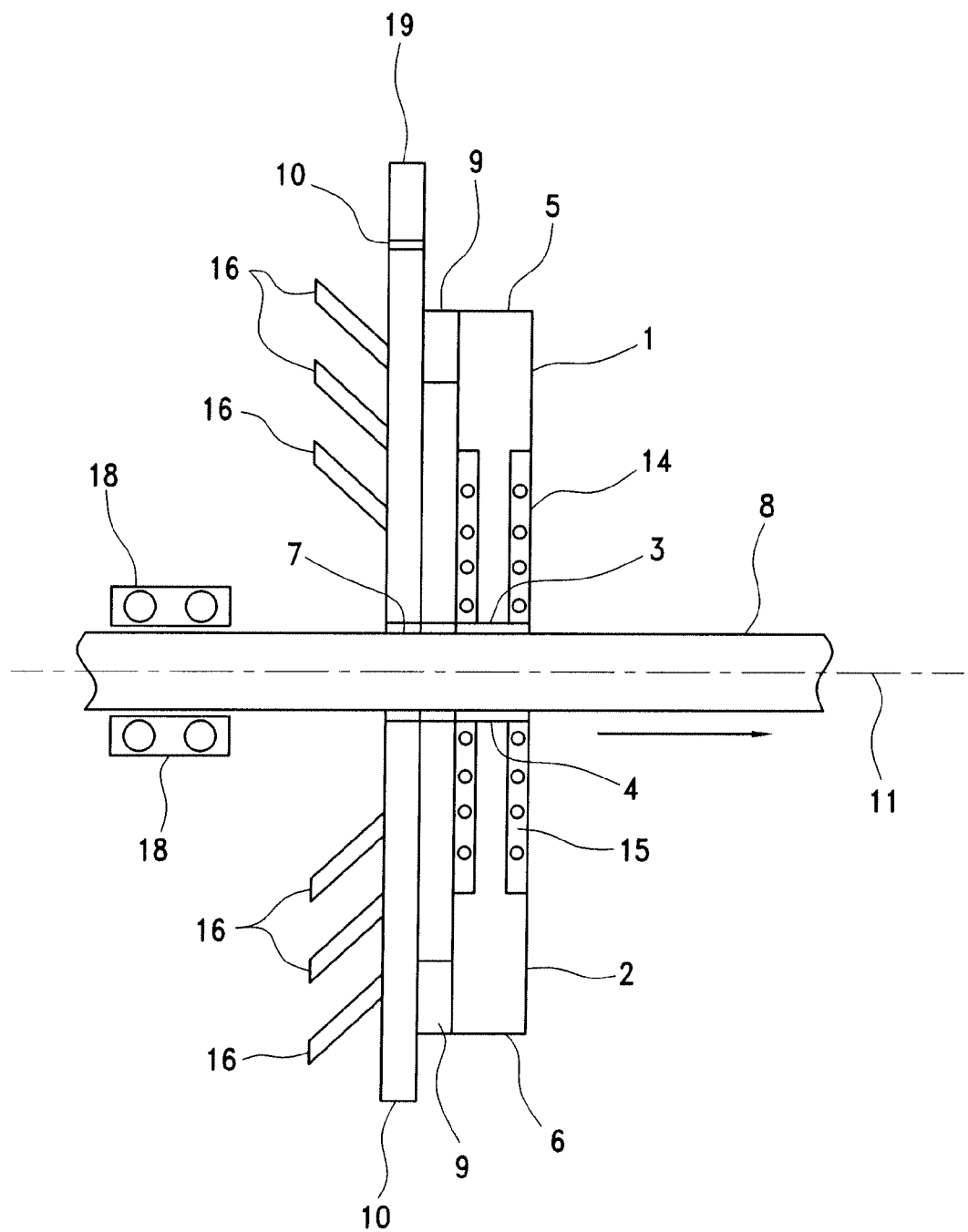
FIG. 2 is a lengthwise sectional view the embodiment of the invention as shown in FIG. 1.

In FIGS. 1 and 2, the two yoke legs 1, 2 are arranged vertically opposite one another such that, between their opposing ends 3, 4, a gap 7 is formed through which a test specimen 8 is guided perpendicular to the plane of the FIG. 1 (in the direction of the arrow in FIG. 2). The exciter windings 14, 15 sit on the gap-forming ends 3, 4 of the yoke legs 1, 2. The outside ends 5, 6, opposite the gap-forming ends 3, 4 are connected via an annular magnetic flux conductor 9 which sits on a rotating disk 10. On the magnetic flux conductor 9, there are two levers 12 which can be pivoted around an axis 17 and on each of which a respective induction coil 13 sits. To adapt to test specimens of different cross section, the yoke legs 1, 2 can be movably mounted on an annular magnetic flux conductor 9 in the direction of the double arrows and to be fixed in the desired position.

The yoke legs 1, 2 and the magnetic flux conductor 9 are preferably produced from a powder material. On the back of the rotating disk 10, for better heat dissipation, there are cooling means (which are not visible in FIG. 1), for example, cooling louvers 16. To test the test specimen 8 for faults, the rotating disk 10 with the magnetic flux conductor 9, the yoke legs 1, 2 and the levers 12 with the induction probes 13, is turned around the lengthwise axis 11 of the test specimen 8 (in the direction of the arrow at the top of FIG. 1) by means of a rotary drive 19 which is shown only symbolically for the sake of clarity, while the test specimen 8, for example, a bar, is guided in a mill train perpendicular to the plane of rotation of the rotary disk 10. In this way, the test specimen 8 is scanned helically to test its quality.

FIG. 2 shows the test specimen 8 guided through the gap 7 by means of a schematically shown feed means 18 in the direction of the arrow while, at the same time, the rotary disk 10, with the yoke legs 1, 2 and the magnetic flux conductor 9, rotates around the lengthwise axis 11 of the test specimen 8 driven by the rotary drive 19 which is shown only symbolically for the sake of clarity. On the back of the rotating disk 10 sit cooling louvers 16 for cooling the yoke legs 1, 2 and the magnetic flux conductor 9. The illustrated special configuration of the magnetic circuit relative to the test specimen 8 yields the decisive advantage that, in the case of an eccentric position of the test specimen, the effective air gap between it and the yokes is practically constant and independent of the rotary position of the rotating disk 10. In this way, the amplitude fluctuation of the fault signal to be otherwise observed is greatly reduced.

The invention is especially well suited to testing of test specimens by means of high-energy magnetic alternating fields, because the high heat losses produced in this process are adequately dissipated in the device in accordance with the invention.

The invention claimed is:

1. Device for testing a test specimen for surface faults, comprising:
   induction probe measurement sensors;
   magnetization means for delivering a magnetic flux into a test specimen by means of the measurement sensors,
   at least two yoke legs having opposed ends, between which a gap is formed through which the test specimen is guided, each of the opposed gap-forming ends having an exciter coil thereon, the exciter coils on the opposed gap-forming ends being oppositely poled, and
   a magnetic flux conductor connecting outside ends of the at least two yoke legs which are opposite the gap-forming ends so that magnetic flux runs through the test specimen perpendicular to a lengthwise direction thereof.

2. Device as claimed in claim 1, wherein at least one of the yoke legs and the magnetic flux conductor are made of a powder composite material.

3. Device as claimed in claim 1, wherein the magnetic flux conductor is annular.

4. Device as claimed in claim 3, wherein the yoke legs movable in a radial direction of the magnetic flux conductor to adapt the size of gap to test specimens of different cross-sectional dimensions and is fixable at various positions to which the yoke legs are movable.

5. Device as claimed in claim 1, wherein the magnetic flux conductor is connected to the outside ends of the yoke legs.

6. Device as claimed in claim 5, wherein the magnetic flux conductor rests on the outside ends of the yoke legs.

7. Device as claimed in claim 1, wherein the yoke legs and the magnetic flux conductor are located on a rotatable disk, and wherein a rotary drive is provided for rotating said disk.

8. Device as claimed in claim 7, wherein the magnetic flux conductor is connected in a highly heat conductive manner to the rotary disk.

9. Device as claimed in claim 8, wherein cooling means for dissipating heat to the environment are provided on the rotatable disk.

10. Device as claimed in claim 9, wherein the cooling means comprise cooling louvers.

11. Device as claimed in claim 1, wherein the induction probe measurement sensors comprise induction coils which sit on pivotable levers.

12. Device as claimed in claim 11, wherein the levers are pivotally mounted on the magnetic flux conductor.

13. Device as claimed in claim 1, wherein additional pairs of yoke legs are provided on the magnetic flux conductor.

14. Device as claimed in claim 13, wherein the yoke legs movable in a radial direction of the magnetic flux conductor to adapt the size of gap to test specimens of different cross-sectional dimensions and is fixable at various positions to which the yoke legs are movable.

* * * * *